United States Patent
Corso, Jr. et al.

[11] Patent Number: 5,913,897
[45] Date of Patent: *Jun. 22, 1999

[54] ENDOPROSTHESIS HAVING MULTIPLE BRIDGING JUNCTIONS AND PROCEDURE

[75] Inventors: Philip P. Corso, Jr., Dublin, Calif.;
Norman F. Williams, Jr., Miami, Fla.

[73] Assignee: Cordis Corporation, Miami Lakes, Fla.

[*] Notice: This patent is subject to a terminal disclaimer.

[21] Appl. No.: 08/955,027

[22] Filed: Oct. 21, 1997

Related U.S. Application Data

[63] Continuation-in-part of application No. 08/491,279, Jun. 16, 1995, Pat. No. 5,716,396, which is a continuation of application No. 08/123,440, Sep. 16, 1993, abandoned.

[51] Int. Cl.$^6$ .......................................................... A61F 2/06
[52] U.S. Cl. ................................................................ 623/1
[58] Field of Search ...................................... 623/1, 11, 12

[56] References Cited

U.S. PATENT DOCUMENTS

| | | |
|---|---|---|
| 4,503,569 | 3/1985 | Dotter . |
| 4,553,545 | 11/1985 | Maass et al. . |
| 4,580,568 | 4/1986 | Gianturco . |
| 4,649,922 | 3/1987 | Wiktor . |
| 4,655,771 | 4/1987 | Wallsten . |
| 4,733,665 | 3/1988 | Palmaz . |
| 4,739,762 | 4/1988 | Palmaz . |
| 4,776,337 | 10/1988 | Palmaz . |
| 4,800,882 | 1/1989 | Gianturco . |
| 4,830,003 | 5/1989 | Wolff et al. . |
| 4,856,516 | 8/1989 | Hillstead . |
| 4,886,062 | 12/1989 | Wiktor . |
| 4,913,141 | 4/1990 | Hillstead . |
| 4,922,905 | 5/1990 | Strecker . |
| 4,969,458 | 11/1990 | Wiktor . |
| 4,994,071 | 2/1991 | MacGregor . |
| 5,015,253 | 5/1991 | MacGregor . |
| 5,019,085 | 5/1991 | Hillstead . |
| 5,019,090 | 5/1991 | Pinchuk . |
| 5,035,706 | 7/1991 | Giantureo et al. . |
| 5,037,427 | 8/1991 | Harada et al. . |
| 5,041,126 | 8/1991 | Gianturco . |
| 5,092,877 | 3/1992 | Pinchuk . |
| 5,133,732 | 7/1992 | Wiktor . |
| 5,135,536 | 8/1992 | Hillstead . |
| 5,161,547 | 11/1992 | Tower . |
| 5,304,200 | 4/1994 | Spaulding . |
| 5,314,472 | 5/1994 | Fontaine . |
| 5,354,309 | 10/1994 | Schnepp-Pesch et al. . |
| 5,370,683 | 12/1994 | Fontaine . |
| 5,421,955 | 6/1995 | Lau et al. . |
| 5,443,498 | 8/1995 | Fontaine ...................................... 623/1 |
| 5,549,663 | 8/1996 | Cottone, Jr. . |
| 5,601,539 | 2/1997 | Corso, Jr. . |
| 5,653,747 | 8/1997 | Dereume ...................................... 623/1 |
| 5,716,393 | 2/1998 | Lindenberg ................................. 623/1 |

FOREIGN PATENT DOCUMENTS

| | | |
|---|---|---|
| 556850 | 2/1992 | European Pat. Off. . |
| 565251 | 10/1993 | European Pat. Off. . |
| 686379 | 12/1995 | European Pat. Off. . |

*Primary Examiner*—Michael J. Milano
*Attorney, Agent, or Firm*—Lockwood, Alex, Fitzgibbon & Cummings

[57] ABSTRACT

An endoprosthesis is provided which presents an endoprosthesis body of a plurality of full-circle helical sections exhibiting a repeating pattern of undulations that follow a generally helical axis. Adjacent full-circle windings each have at least one bridging junction joining together apex-like portions of adjacent full-circle sections. In a preferred arrangement, a plurality of these bridging junctions define a substantially in-line helical pattern of bridging junctions along the endoprosthesis or stent. One, two, three or more of these substantially in-line helical patterns can be provided. Also provided is a procedure by which the endoprosthesis or stent is implanted by deployment with a suitable device, the deployment expanding the pattern of undulations in a uniform manner to provide an especially consistent support surface throughout the endoprosthesis.

24 Claims, 6 Drawing Sheets

ENDOPROSTHESIS HAVING MULTIPLE BRIDGING JUNCTIONS AND PROCEDURE

CROSS-REFERENCE TO RELATED APPLICATION

This is a continuation-in-part of application Ser. No. 08/491,279, filed Jun. 16, 1995, now U.S. Pat. No. 5,716,396, which is a continuation of application Ser. No. 08/123,440, filed Sep. 16, 1993, now abandoned.

DESCRIPTION

BACKGROUND AND DESCRIPTION OF THE INVENTION

The present invention generally relates to endoprostheses, also known as stents, and to their preparation and use. More particularly, the invention relates to endoprostheses having multiple junctions which join adjacent windings composed of undulating bendable segments which are oriented in a generally helical pattern along the length of the endoprosthesis. The bendable segments impart radial expandability to the endoprosthesis, which can be tailored so as to vary the hoop strength of the endoprosthesis while still retaining the ability of the endoprosthesis to follow the contour of the vessel within which it is to be deployed. Endoprostheses according to the invention also exhibit exceptional uniformity of expansion and maintain the desired solid surface area percentage substantially throughout the entirety of the endoprosthesis, particularly after deployment.

Various endoprosthesis devices or stents have been developed or proposed for use in association with angioplasty treatments and other medical treatments or procedures wherein devices having expandable components, such as balloon catheters, are used to treat a condition with a body vessel. The endoprosthesis or stent is in the nature of a device, usually tubular or cylindrical in shape, which is deployed by a balloon or otherwise, such as self-expansion, and which remains within the vessel at a treatment location upon withdrawal of the balloon catheter or other deployment and/or treatment device.

Exemplary patents in this regard include Pinchuk U.S. Pat. Nos. 5,019,090 and 5,092,877, MacGregor U.S. Pat. Nos. 4,994,071 and 5,015,253, Hillstead U.S. Pat. Nos. 4,856,516 and 4,913,141, and Gianturco U.S. Pat. Nos. 4,580,568 and 4,800,882. Certain endoprostheses or stents, such as those illustrated in Dotter U.S. Pat. No. 4,503,569, Wallsten U.S. Pat. No. 4,655,771 and Palmaz U.S. Pat. No. 4,733,665 present devices which have very limited compliance characteristics. They are not, for example, particularly well-suited for "stenting" body passageways having configurations which are not substantially linear. For example, stenting curved vessel pathways with endoprostheses that present a generally rigid cylindrical shape typically requires endoprostheses that are very short in length and that are strung out along the curved pathway, with each such endoprosthesis engaging an adjacent endoprosthesis along respective edges of the endoprostheses, thereby leaving a gap between each pair of endoprostheses at the outside radius of the curved vessel being stented. Also, such endoprostheses often will be delivered separately, thereby increasing the invasiveness of the procedure. In other endoprostheses, concerns can be raised that the body of the endoprosthesis stretches along its longitudinal axis during use. For example, Wiktor U.S. Pat. No. 5,133,732 proposes longitudinal over-stretch limiting means such as by attaching a longitudinal wire generally parallel to the axis of the endoprosthesis.

Accordingly, previous approaches in the endoprosthesis or stent art have proposed or provided devices having good hoop strength, which can be particularly important in stenting applications which could be subjected to forces tending to collapse the endoprosthesis, such as when relatively large vessels are stented or when the stent is deployed within a vessel susceptible to external forces, such as within the leg. Other known endoprostheses or stents exhibit less hoop strength but are more compliant in that they are better suited to conform to the contour of the vessel, rather than being so non-conforming as to mis-shape the vessel after deployment. A typical disadvantage of the more-compliant stent devices is that they tend to deform upon or after deployment and present stenting surfaces which can lack desirable uniformity throughout the working surface area of the stent. Development of non-uniformity in the working surface area of the stent can be especially evident during expansion of the stent from its collapsed, insertion diameter to its expanded, implanted diameter. At times, for balloon-deployed stents, this lack of uniformity upon expansion is exacerbated by folds or other non-uniformities in a balloon on which the stent is mounted for deployment.

It has been found that the endoprostheses in accordance with the present invention exhibit the ability to follow the contour of the vessel being stented while still exhibiting the hoop strength needed for adequate support such as that provided by less compliant structures including those as discussed herein, while providing the additional advantage of ensuring uniform expansion to provide an expanded stent that exhibits the desired percentage of support surface area. Furthermore, with the present invention, these important properties can be tailored to fit the particular needs of the problem being addressed by varying compliance and hoop strength as needed.

In summary, the present invention achieves these advantages and advances the endoprosthesis art by an endoprosthesis constructed of a plurality of bendable segments organized in an undulating and substantially uniform fashion having a generally helical configuration. The endoprosthesis body is thus composed of a plurality of full-circle undulating sections continuous with each other along the helical path. In general, the undulations of adjoining full circle sections generally line up with one another to either contact one another or be closely spaced from one another. At selected ones of these locations, bridges are provided in order to thereby join adjacent sections. At least one bridge is positioned along each full-circle section. In an especially preferred embodiment, the bridges are oriented with respect to each other so as to form a helical pattern of bridges along the endoprosthesis.

It is accordingly a general object of the present invention to provide an improved endoprosthesis having multiple bridged junctions and to make and use same.

Another object of the present invention is to provide an improved endoprosthesis or stent that exhibits good strength while having the ability to follow the contour of the vessel within which it is implanted.

Another object of this invention is to provide an improved endoprosthesis that minimizes the risk of developing intimal hyperplasia or irritation brought on by its deployment within a living vessel and the method associated therewith.

Another object of the present invention is to provide an improved endoprosthesis and deployment procedure whereby the stent overlaps by at least about 0.5 cm both sides of a dissection being treated, even in the case of an elongated dissection that does not exhibit a straight contour.

Another object of this invention is to provide an improved endoprosthesis and method to provide a stent which has an integrity comparable to that of a much less flexible stent while still exhibiting flexibility required in many uses, including within coronary vessels.

Another object of the present invention is to provide an endoprosthesis having multiple bridged junctions which exhibit a flexibility reduced by only about 10 to 15% of a similar device without bridged junctions and while simultaneously providing the integrity of stent structures exhibiting much less flexibility or compliance properties.

Another object of this invention is to provide an improved stent or endoprosthesis and use thereof with exceptional uniformity in presentation of supporting surface area throughout the working surface of the stent.

Another object of the present invention is to provide an improved endoprosthesis or stent which reduces in length when expanded during deployment, while increasing the pitch of the helix that broadly defines the configuration of the endoprosthesis.

Another object of the present invention is to provide an improved endoprosthesis or stent which, when deployed, avoids overlap of stent structural components to thereby provide a stent having minimal thickness throughout the stent to reduce the likelihood of accelerated hyperproliferation or thicker cell growth as a protection response to a thickened wall surface.

Another object of the present invention is to provide endoprostheses and manufacture thereof while tailoring same for desired end uses, including vascular, bronchial, tracheal, urological, rectal, transinterhepactic shunting, bilary tree, and the like.

Another object of this invention is to provide an improved endoprosthesis having multiple bridged junctions which substantially reduce external expansion of a stent when deployed within vessels having curved contours.

These and other objects, features and advantages of this invention will be clearly understood through a consideration of the following detailed description.

BRIEF DESCRIPTION OF THE DRAWINGS

This invention is further elucidated in the following description with reference to the annexed drawings, wherein.

DESCRIPTION OF THE PARTICULAR EMBODIMENTS

Figure 1:
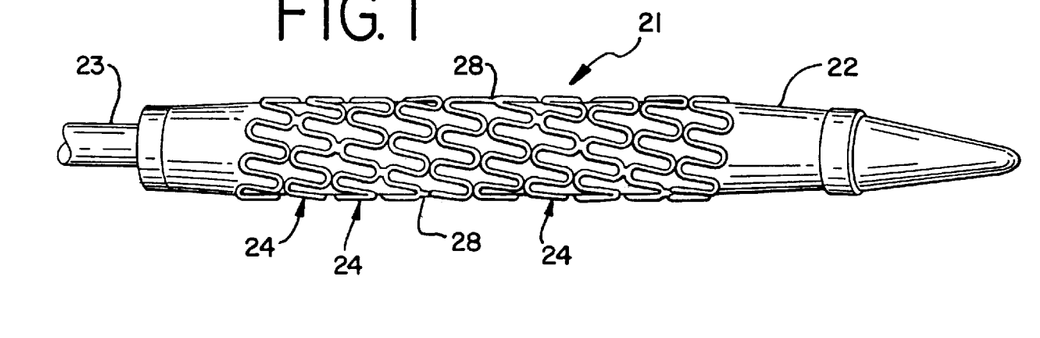
FIG. 1 is a perspective view of a portion of a balloon catheter having an endoprosthesis in accordance with the present invention positioned thereon for subsequent deployment.

FIG. 1 depicts an endoprosthesis or stent in accordance with the present invention, generally designated as 21, positioned over a balloon component 22 of a catheter 23 of generally known construction. The balloon is illustrated in a deflated condition, with the tube-like endoprosthesis closely lying thereover. As is well known in the art, when a suitable fluid such as saline solution is passed into the catheter under pressure, the balloon component 22 expands, thereby radially expanding the endoprosthesis 21. Typically, this expansion is carried out within a body vessel, such as within a blood vessel, coronary passageway, bilary duct or other body vessel.

The expansion is initiated after the balloon and endoprosthesis are positioned within the vessel so as to be radially spaced away from a diseased or damaged area of the vessel. Upon radial expansion as described, the balloon deploys the endoprosthesis to engage and support the diseased or damaged portion. It has been found that the effectiveness of this stenting procedure is particularly enhanced when the endoprosthesis traverses a length greater than the length of the diseased section so that there is an overlap of at least about 0.5 cm of endoprosthesis beyond each end of the diseased or damaged sections. Accordingly, the deployment procedure according to the invention includes providing an endoprosthesis having a length greater than the length of the diseased area when the endoprosthesis is positioned along the diseased area, taking into consideration changes in contour of the vessel at the diseased section.

With more particular reference to the endoprosthesis 21, the illustrated embodiments begin as a tube of metal or polymer material, and patterned portions of same are removed to provide a tube-like member having strands and/or webs as shown. The thus formed endoprostheses can be suitable for self-expansion or for deployment with a balloon catheter or the like.

concerning especially the latter type, these endoprostheses exhibit malleability adequate to be formed into shapes such as those illustrated, retain those shapes, and expand as discussed herein when subjected to radial outwardly directed forces. In the illustrated embodiments, the endoprosthesis has bendable segments to provide a repeating pattern of undulations. The undulations are shaped into a plurality of full-circle sections 24 which extend through 360°. Each section 24 includes a plurality of bendable segments 25. Each bendable segment includes legs 26 joined by a connecting portion 27. In the embodiment shown in the drawings, legs 26 and connecting portions 27 define a sinusoidal curve which can be shaped as illustrated in the drawings or take on somewhat different shapes.

A plurality of bridges, junctions or bridged junctions 28 integrally join adjacent pairs of connecting portions 27. Preferably, the components of the endoprosthesis are integrally formed from a length of tubing, typically of hypotubing size. Such is achieved by removing portions of the hypotubing in a designed pattern so as to leave the endoprosthesis strand and web components, including the bendable segments, legs and connecting portions for each full-circle section. The removing can be by any suitable approach including chemical etching and/or cutting such as by laser cutting and removal.

Figure 2:
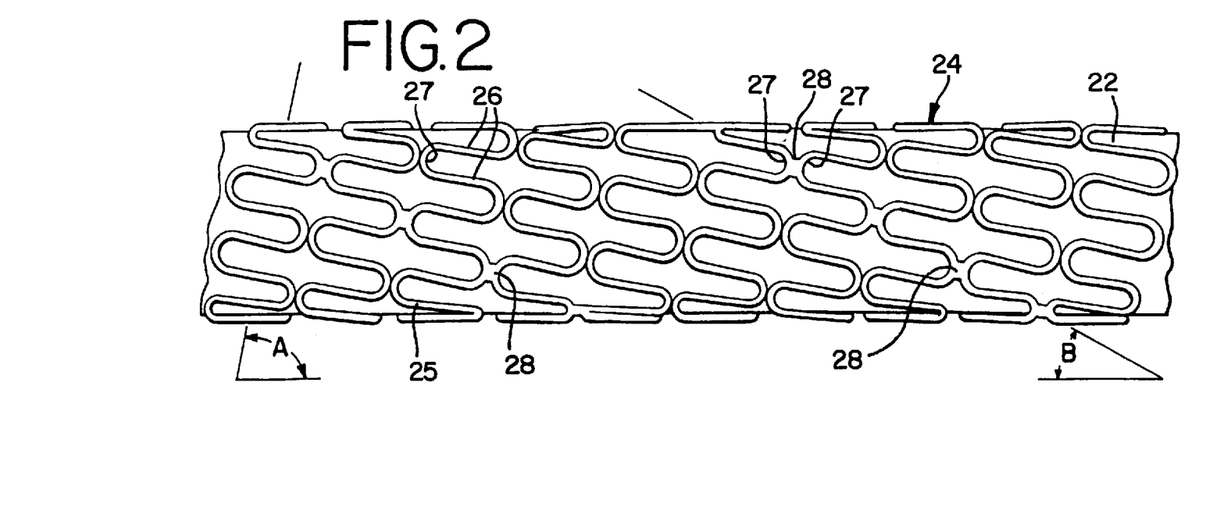
FIG. 2 is a enlarged elevational view illustrating the embodiment shown in FIG. 1 which includes two helically oriented spines defined by a plurality of bridged junctions positioned along the endoprosthesis.
Figure 4:
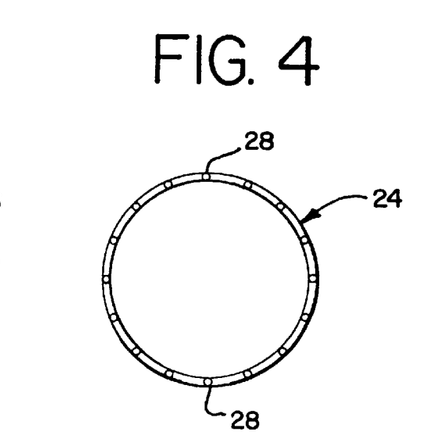
FIG. 4 is an end view of the embodiment shown in FIG. 2.

In accordance with the invention, at least one bridged junction 28 joins each full-circle section 24 to the section or sections adjacent thereto. While the helix orientation angle "A" of the sections as shown in FIG. 2 is relatively steep with respect to the longitudinal axis of the endoprosthesis 21, the pitch angle "B" of the plurality of bridges 28 is relatively shallow. It will be noted that pitch angle "B" follows the pitch angle defined by adjacent connecting portions 27 of adjacent sections 24. Accordingly, the pitch angle "B" of the illustrated helical bridge pattern follows the pitch angle of the helix that is defined by adjacent connecting portion pairs. As perhaps best illustrated in FIG. 4, this embodiment includes two such generally helical bridge patterns which generally parallel each other and which are longitudinally spaced from one another.

Figure 3:
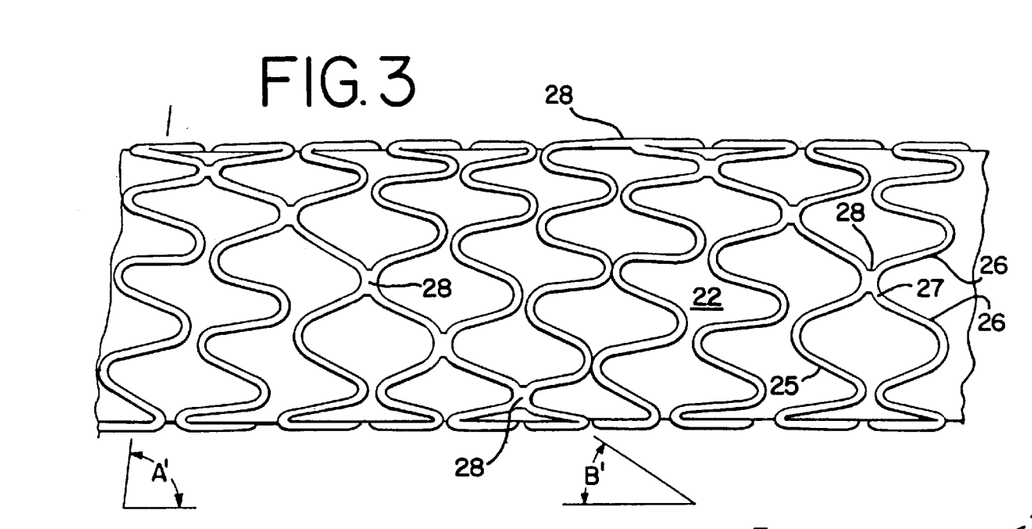
FIG. 3 is an elevational view of the embodiment shown in FIG. 2 wherein the endoprosthesis has been expanded for deployment.

It will be noted from FIG. 3 that, after expansion, the overall length of the endoprosthesis 21 is decreased, while the helix winding angle "A'" is steeper than that of the helix winding angle "A" prior to expansion, and the pitch angle "B'" after expansion is steeper than the pitch angle "B" prior to expansion. For example, a particular size of such an endoprosthesis can have an unexpanded diameter of 8 mm and an unexpanded length of 3 cm. After a typical expansion to 12 mm, its length is about 2.7 cm, with the helix orientation angle and pitch angle being changed accordingly.

It will further be noted that each of the bendable segments 25 has opened up to substantially the same extent, with each leg 26 being spaced farther from each of its adjoining legs than prior to expansion, this opened spacing being substantially uniform throughout each winding of the endoprosthesis. Each bridged junction 28 remains along the helical pathway even after the endoprosthesis is expanded. This can be generally referred to as sinusoidal expansion which the invention achieves even with pleated balloons that can tend to cause non-sinusoidal expansion of other stents, wherein one leg of the bendable segment expands readily while its other leg movement is dampened.

Figure 8:
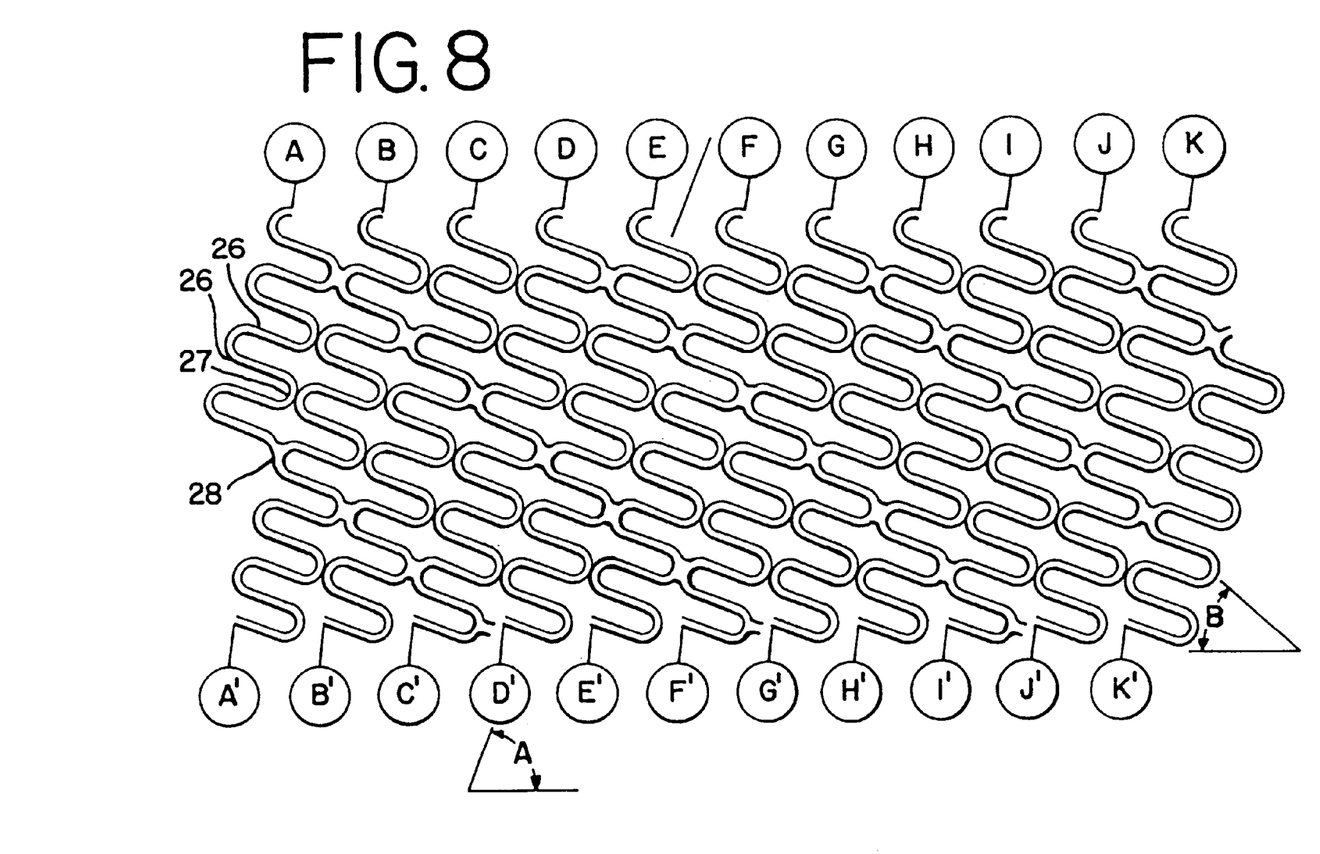
FIG. 8 is a schematic illustration of the embodiment shown in FIGS. 1 through 4 wherein the endoprosthesis has been severed longitudinally and flattened for illustrative purposes.
Figure 9:
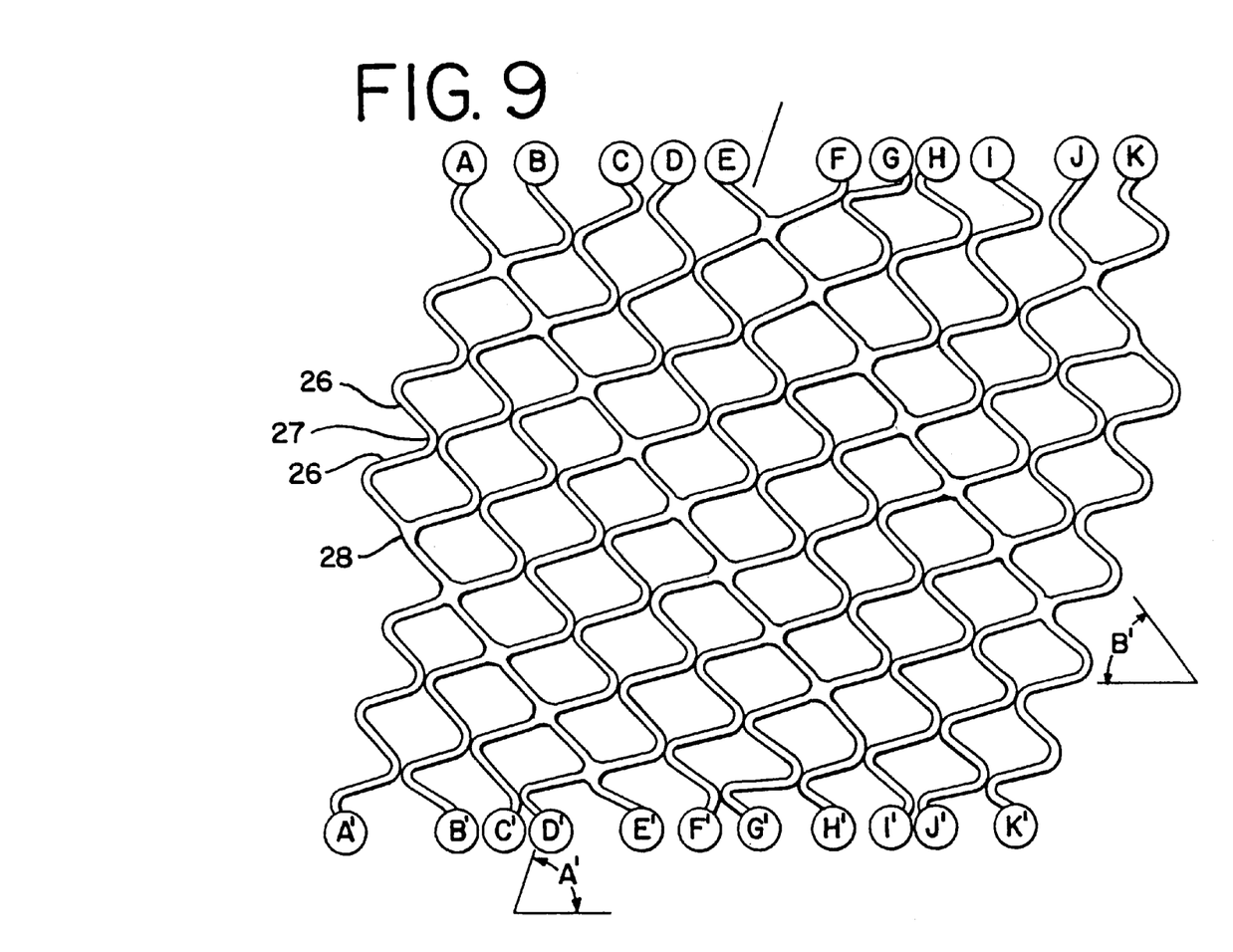
FIG. 9 is a schematic view as shown in FIG. 8 in its expanded orientation.

Because of this uniform type of expansion, the unexpanded as well as the expanded supporting surface area of the endoprosthesis is substantially consistent throughout the endoprosthesis. This is perhaps even better illustrated in the flattened depiction of this embodiment which is shown in FIG. 8 and FIG. 9 without the optical distortion present in the other figures due to the curvature of the cylindrical endoprosthesis. For example, FIG. 9 shows the uniform nature of the expanded supporting surface area.

Figure 5:
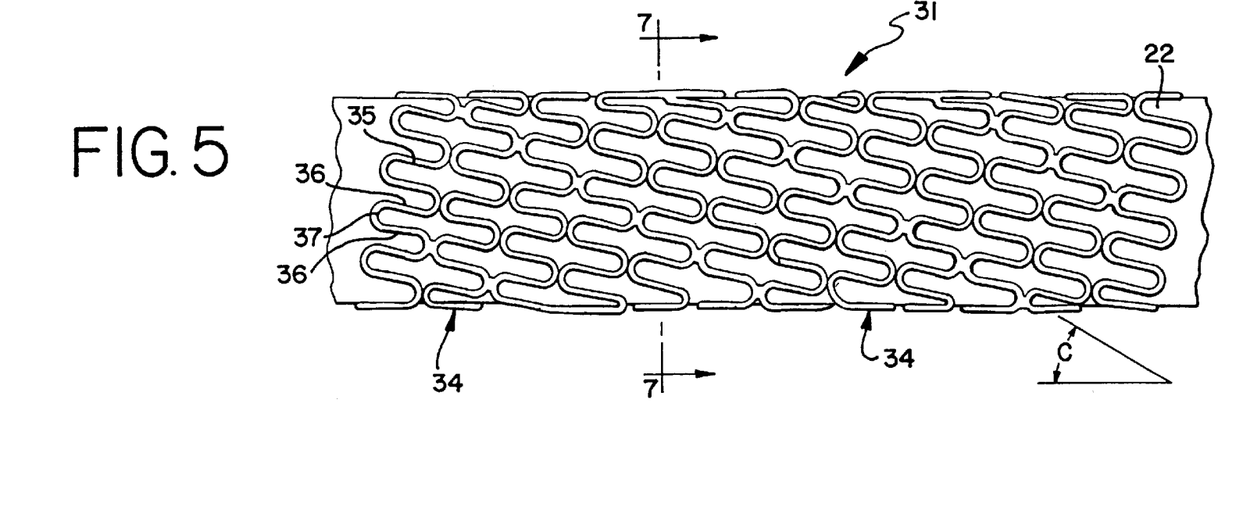
FIG. 5 is an elevational view of another embodiment of the present invention having three separate helically oriented spines defined by a plurality of bridged junctions aligned along three generally helical paths.
Figure 6:
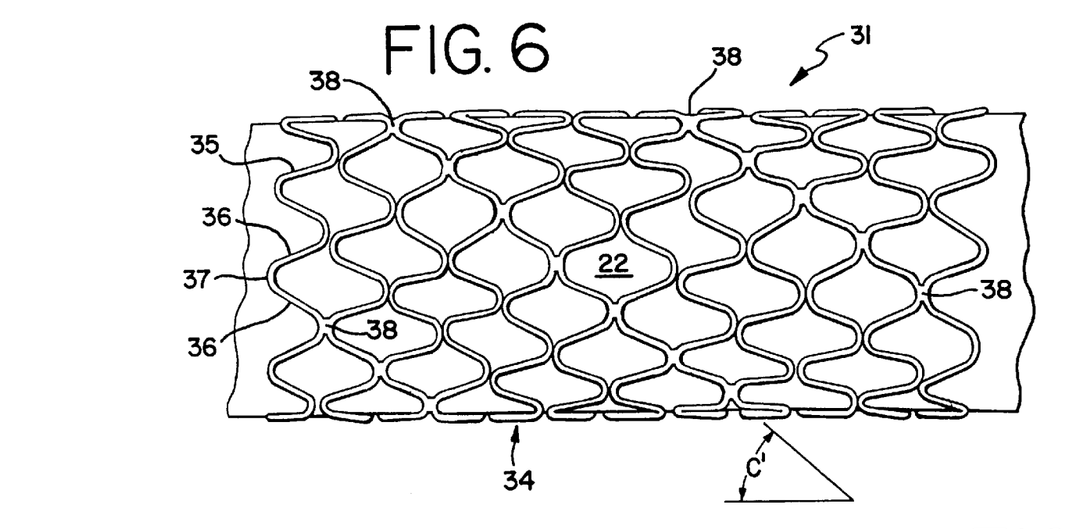
FIG. 6 is an elevational view of the embodiment illustrated in FIG. 5 shown in its expanded position for deployment.
Figure 7:
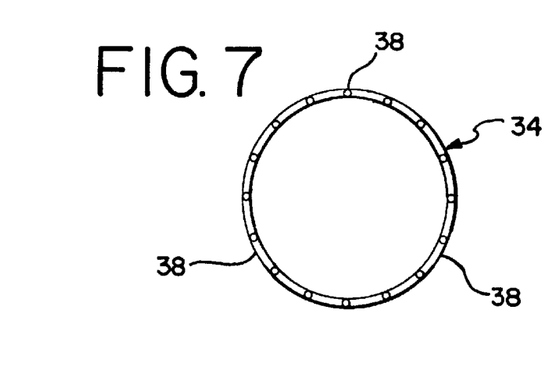
FIG. 7 is an end view of the embodiment illustrated in FIG. 5.

With reference to the embodiment illustrated in FIGS. 5, 6 and 7, endoprosthesis or stent 31 is composed of a plurality of full-circle sections 34 having a plurality of bendable segments 35 having legs 36 and a connecting portion 37. In this embodiment, bridged junctions 38 are aligned along three helical pathways which follow pitch angle "C" when unexpanded as illustrated in FIG. 5 and pitch angle "C'" as illustrated in FIG. 6.

In these illustrated embodiments, thirteen bridge junctions are provided for each inch (2.54 cm) of length of endoprosthesis per helical pathway or "spine." Accordingly, in the two helix or "double spine" embodiment illustrated in FIGS. 1 through 4, twenty-six bridged sections are provided for each longitudinal inch (2.54 cm) of endoprosthesis. In the three helix or "triple spine" embodiment illustrated in FIGS. 5, 6 and 7, there are thirty-nine bridged junctions per longitudinal inch (2.54 cm) of endoprosthesis, and the initial tube can be larger than for the double spine embodiment.

Figure 10:
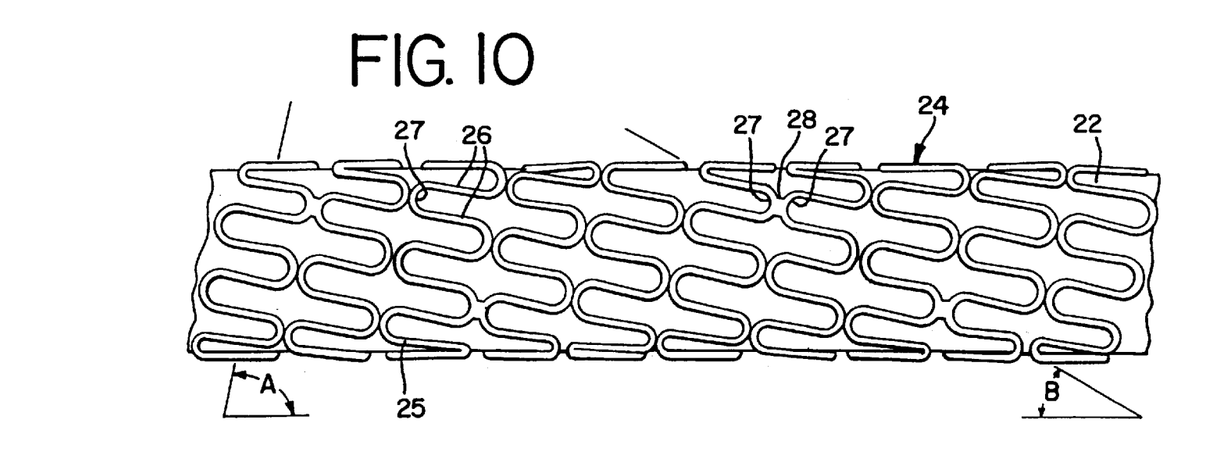
FIG. 10 is an elevational view showing an embodiment which includes an in-line helical pattern or in-line helical patterns including bridging junctions alternating with adjacent bendable connecting portions which are not joined together.
Figure 11:
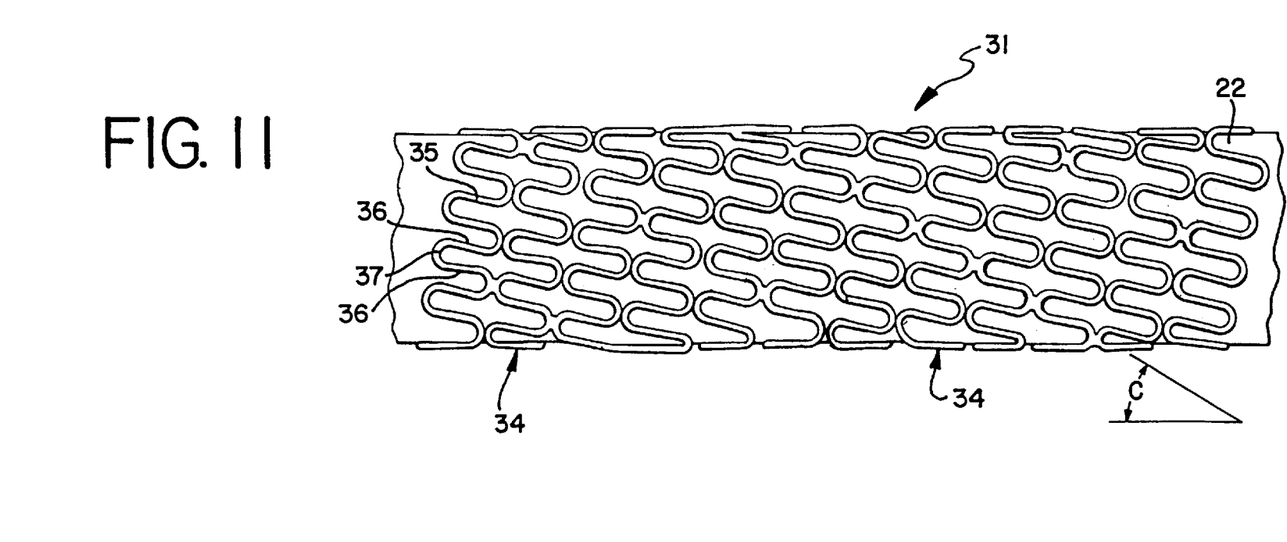
FIG. 11 is an elevational view illustrating an embodiment which includes a plurality of substantially in-line helical patterns which have bridging junctions alternating with adjacent bendable connecting portions which are not joined together.

While the illustrated preferred embodiments show the plurality of bridged junctions oriented in a helical manner along a generally continuous pathway or helical spine, other bridged junction orientations are also possible. For example, one of the spines of a multiple-spine configuration can omit bridged junctions therealong, such that every other adjacent pair of connecting portions along this interrupted helical spine can remain unattached to each other. Again, in a multiple-spine configuration, alternating connecting portion adjacent pairs can remain unattached to each other, preferably staggered in such a manner that each adjacent section is joined together at its other adjacent section or sections by at least one bridge at a connecting portion pair. Examples of these types of substantially in-line helical patterns which include bridging junctions 28 alternating with adjacent bendable connecting portions 27 are illustrated in FIG. 10 and in FIG. 11. It is possible to form helical spines in an orientation other than that as illustrated which follows the pitch angle of the helical orientation, for example bridge spine patterns which are generally parallel to the axis of the endoprosthesis and bridge spine patterns which follow a counter-clockwise oriented helix, rather than the clockwise oriented helical spine illustrated in the drawings. In addition, although the drawings illustrate endoprostheses having two or three in-line bridge spine patterns, patterns having a single spine and having four or more spines are also possible.

The embodiments illustrated in the drawings are preferred, primarily because of the uniform expansion experienced when these endoprostheses are deployed. By following the pitch angle of the helix configuration of the endoprosthesis, and by providing bridge spine patterns that provide a bridged junction at each connecting portion pair therealong, a particularly even pull is experienced on each leg 26, 36 when the endoprosthesis is expanded or expands during deployment. Particularly uniform stretching is experienced, which is important to the operative functional advantages of the endoprostheses according to the invention.

More specifically, it is at present generally accepted that the supporting surface area (typically the "metal" outside or working surface of the stent) is to constitute between about 12% and about 15% of the cylindrical surface defined by the stent. Otherwise, inadequate support will be provided. This means that, under present beliefs, it is desirable to have between about 85% and about 88% open space presented by the external cylindrical definition of the stent. The configuration of the stent of the invention is tailored to fall within these guidelines. More importantly, the present invention provides a structure wherein the amount of supportive surface area or "metal" presented to the vessel by the stent is a consistent percentage throughout the length and circumference of the stent. Accordingly, if 12 to 15% supporting surface area is provided by the stent, all portions of the stent surface, both before expansion and when expanded as deployed, presents a supporting surface area within this percentage range. This uniformity of supporting surface is important. This feature, for example, avoids the undesirable situation where a stent might meet the 12 to 15% guideline when the entirety of the stent surface is averaged, but might be considerably below the guideline percentage at the very location along the stent where support is most needed. Similarly, if certain locations of the stent present too great a percent of support surface or metal, accelerated hyperproliferation could occur, resulting in cell growth that is thicker than desired at these locations of excess support surface, resulting in a narrowing of the body passageway at this location.

Endoprostheses made in accordance with the present invention are also particularly well-suited for deployment within vessels having curved contours. It will be appreciated that the combination of unattached connecting portion pairs and bridged connecting portion pairs permit the endoprosthesis to lie within and follow a curve in a vessel without presenting excessive spacing between unattached connecting portion pairs, for example at an outside or larger radius curve. It has been found that, in similar stent structures without the pattern of bridged connections, the outside curve of the endoprosthesis will open about two times to three times the spacing between adjacent windings when unexpanded and longitudinal. The present invention dampens that expansion by at least approximately 60% to 70% while still permitting the endoprosthesis to follow the natural contour of the vessel. This results in a marked reduction in excess free space presented by the outside curve of the endoprosthesis. In addition, the pattern of bridged connections helps to prevent excessive overlap of endoprosthesis material at the inside curve of the vessel contour.

With more particular reference to the material out of which the endoprostheses according to the invention are made, this typically will vary depending upon whether the stent is to be expanded or to be self-expanding. In the former instance, the material should have malleability characteristics. Included are tantalum, stainless steel, titanium, silver, gold, annealed elastic metal materials, and alloys containing same. Polymers may also be used, such as polyether sulfone, polyimides, polycarbonates, polypropylenes, high molecular weight polyethylenes, carbon fibers, Kevlar (trademark) polymer, and the like. Self-expanding stents may be made from materials having spring-like resiliency, such a stent being formed from a tube having a diameter on the order of the deployed diameter, and this stent-configured tube is compressed circumferentially and placed in a deployment tool, often a cylinder-like device. Upon deployment in the body, the stent springs radially outwardly as it exits the deployment tool. A preferred material for this self-expanding embodiment is a superelastic alloy. Typical in this regard are alloys having large percentages of nickel and titanium. Such alloys have austentic properties which do not effect a shape change during normal temperatures to which the stent is subjected during use. Materials suitable for this use have exceptional spring-back resiliency properties, and stents of the present structure made from such materials spring open once released from the deployment tool, typically so as to return to approximately the diameter of the initial tube from which the stent was formed.

It is also possible to coat the stent with porous or textured surfaces for cellular ingrowth and the like or with non-thrombogenic agents such as pyrolytic carbon, heparin, hydrogels, Teflon (trademark) materials, silicones, polyurethanes and the like. Treatments can also be carried out so that drugs or medicines can be eluted therefrom. It is also possible that certain stents may be made of biodegradable materials. The stent material must, of course, be biocompatible.

It will be understood that the embodiments of the present invention which have been described are illustrative of some of the applications of the principles of the present invention. Numerous modifications may be made by those skilled in the art without departing from the true spirit and scope of the invention.

We claim:

1. An implantable transluminal endoprosthesis comprising:

a tube-like member having a plurality of full-circle helical sections which extend through 360° and which are substantially continuous with each other along a generally helical axis of the tube-like member;

said tube-like member includes a repeating pattern of undulations which follow said generally helical axis, said pattern of undulations having a plurality of substantially equally sized and shaped bendable segments alternating with bendable connecting portions to impart radial expandability to the endoprosthesis, the endoprosthesis having an unexpanded transluminal insertion circumference and an expanded deployed circumference which is greater than said unexpanded circumference;

said plurality of full-circle helical sections are generally adjacent to each other, and respective ones of said bendable connecting portions of adjacent full-circle helical sections are adjacent to each other so as to define adjacent bendable connecting portions;

said bendable segments are positioned in a generally closed orientation with respect to each other at said unexpanded circumference and in a generally opened orientation with respect to each other and with respect to said bendable connecting portions at said expanded circumference; and a plurality of bridging junctions join less than all of said adjacent bendable connecting portions of adjacent full-circle helical sections to each other, said bridging junctions being present along the length of the tube-like member, each of said full-circle helical sections has at least one of said plurality of bridging junctions, and the remainder of said adjacent bendable connecting portions are not joined together.

2. The endoprosthesis in accordance with claim 1, wherein said plurality of bridging junctions define a substantially in-line helical pattern including said bridging junctions.

3. The endoprosthesis in accordance with claim 2, wherein said substantially in-line helical pattern includes bridging junctions alternating with ones of said adjacent bendable connecting portions which are not joined together.

4. The endoprosthesis in accordance with claim 1, wherein said plurality of bridging junctions define two substantially in-line helical patterns of bridging junctions along the endoprosthesis, said helical patterns of bridging junctions being longitudinally spaced from each other.

5. The endoprosthesis in accordance with claim 4, wherein at least one of said substantially in-line helical patterns includes bridging junctions alternating with ones of said adjacent bendable connecting portions which are not joined together.

6. The endoprosthesis in accordance with claim 1, wherein said plurality of bridging junctions define three substantially in-line helical patterns of bridging junctions along the endoprosthesis, said helical patterns of bridging junctions being longitudinally spaced from each other.

7. The endoprosthesis in accordance with claim 1, wherein said plurality of bridging junctions define a plurality of substantially in-line helical patterns of bridging junctions along the endoprosthesis, said helical patterns of bridging junctions being longitudinally spaced from each other.

8. The endoprosthesis in accordance with claim 7, wherein at least one of said substantially in-line helical patterns includes bridging junctions alternating with ones of said adjacent bendable connecting portions which are not joined together.

9. The endoprosthesis in accordance with claim 1, wherein said endoprosthesis tube-like member has a length which decreases when the endoprosthesis is expanded from said unexpanded circumference to said expanded circumference.

10. The endoprosthesis in accordance with claim 1, wherein said plurality of bridging junctions defines at least one substantially in-line helical pattern of bridging junctions following a pitch angle along the endoprosthesis tube-like member and defined with respect to the longitudinal axis of the tube-like member, and said pitch angle of the in-line helical pattern of bridging junctions increases as the endoprosthesis expands from its unexpanded circumference to its expanded circumference.

11. The endoprosthesis in accordance with claim 10, wherein the generally helical axis of the endoprosthesis tube-like member has a helix winding angle defined with respect to the longitudinal axis of the tube-like member, and said helix winding angle increases as said endoprosthesis expands from said unexpanded circumference.

12. The endoprosthesis in accordance with claim 1, wherein said repeating pattern of undulations defines a generally sinusoidal pattern.

13. The endoprosthesis in accordance with claim 1, wherein said plurality of bendable segments each have a pair of legs which extend from and are integral with one of said bendable connecting portions.

14. The endoprosthesis in accordance with claim 13, wherein each said bridging junction is integral with a pair of said adjacent connecting portions.

15. The endoprosthesis in accordance with claim 14, wherein each said bridging junction also extends between and away from said pair of adjacent bendable connecting portions.

16. The endoprosthesis in accordance with claim 1, wherein said plurality of bendable segments, bendable connecting portions and bridging junctions all lie along a single substantially cylindrical plane defined by the endoprosthesis tube-like member.

17. The endoprosthesis in accordance with claim 1, wherein said plurality of bendable segments each have a pair of legs and wherein said repeating pattern of undulations changes during expansion from said unexpanded circumference to said expanded circumference to define an expanded repeating pattern in which alternating said legs of the bendable segments are generally parallel to each other.

18. The endoprosthesis in accordance with claim 1, wherein the endoprosthesis tube-like member defines an outwardly facing supporting surface area that comprises between about 12% and about 15% of a cylindrical plane defined by the endoprosthesis, the balance of the cylindrical plane being non-supporting open area.

19. The endoprosthesis in accordance with claim 1, wherein said bridging junctions impart increased hoop strength to said endoprosthesis tube-like member while said repeating pattern of undulations and bridging junctions combine to define an endoprosthesis having compliance properties to follow contours of vessels within which the endoprosthesis is implanted.

20. A procedure for transluminally implanting an endoprosthesis, comprising the steps of:

providing a tube-like member having a plurality of full-circle helical sections which extend through 360° and which are substantially continuous with each other along a generally helical axis of the tube-like member, the tube-like member having a repeating pattern of undulations which follow the generally helical axis, the pattern of undulations having a plurality of substantially equally sized and shaped bendable segments alternating with bendable connecting portions to impart radial expandability to the endoprosthesis, the bendable connecting portions of one of the full-circle helical sections are generally adjacent to respective bendable connecting portions of an adjacent full-circle helical section to define a plurality of adjacent pairs of bendable connecting portions;

said providing step includes integrally forming bridging junctions between selected ones of said pairs of connecting portions, said integrally forming step joining at least one, and less than all, of said pairs of connecting portions along each of said adjacent full-circle helical sections to form an endoprosthesis;

positioning the endoprosthesis along a transluminal insertion assembly such that the endoprosthesis is at an unexpanded circumference thereof;

transluminally inserting the transluminal insertion assembly having the endoprosthesis into a body vessel and stopping the inserting step when the endoprosthesis is in general alignment with a diseased portion of the body vessel;

manipulating the transluminal insertion assembly to have the endoprosthesis expand to an expanded circumference thereof to have the endoprosthesis move into supporting engagement with the diseased portion of the body vessel, said step including substantially uniformly opening the repeating pattern of undulations in order to thereby uniformly support the entirety of the diseased portion; and removing the transluminal insertion assembly from the body passageway while leaving the endoprosthesis with its expanded circumference at the diseased portion the body vessel.

21. The procedure in accordance with claim 20, wherein said step by which the endoprosthesis expands to the expanded circumference includes opening the repeating pattern of undulations such that substantially equally sized and shaped bendable segments thereof move apart from one another and exhibit an expanded orientation at which alternating ones of said bendable segments are generally parallel to each other.

22. The procedure in accordance with claim 20, wherein said step of integrally forming includes defining a substantially in-line helical pattern of bridging junctions.

23. The procedure in accordance with claim 20, wherein said step of integrally forming includes forming together a plurality of said pairs of connecting portions to define a plurality of substantially in-line helical patterns of bridging junctions which are generally longitudinally spaced from one another.

24. The procedure in accordance with claim 20, wherein said step by which the endoprosthesis expands presents said endoprosthesis as a supporting surface area making up between about 12 percent and about 15 percent of a cylindrical plane defined by the endoprosthesis when expanded, which supporting surface area percent range is present throughout the tube-like member.

* * * * *